US005203345A

United States Patent [19]

Kennedy et al.

[11] Patent Number: 5,203,345

[45] Date of Patent: Apr. 20, 1993

[54] METHOD OF USING A SUPPORT ANCHOR FOR THE VAGINA OF A MAMMALIAN FEMALE

[75] Inventors: Alma D. Kennedy; Kimberly D. Redden; Tracy L. Gilson, all of Manitoba, Canada

[73] Assignee: University of Manitoba, Winnipeg, Canada

[21] Appl. No.: 784,210

[22] Filed: Oct. 31, 1991

[51] Int. Cl.[5] ............ A61B 5/00

[52] U.S. Cl. ............ 128/736; 128/788

[58] Field of Search ............ 128/736, 738, 785, 786, 128/788

[56] References Cited

U.S. PATENT DOCUMENTS

| | | | |
|---|---|---|---|
| Re. 32,275 | 11/1986 | Zartman . | |
| Re. 32,758 | 10/1988 | Zartman . | |
| 3,811,423 | 5/1974 | Dickinson et al. . | |
| 3,811,424 | 5/1974 | Dickinson et al. . | |
| 3,811,443 | 5/1974 | Dickinson et al. . | |
| 4,091,807 | 5/1978 | Dickinson et al. . | |
| 4,377,157 | 3/1983 | Zartman . | |
| 4,387,724 | 6/1983 | Zartman | 128/736 |
| 4,392,005 | 7/1983 | Mohrman | 128/736 |
| 4,506,679 | 3/1985 | Mann | 128/785 |
| 4,616,640 | 10/1985 | Kaali et al. | 128/788 |
| 4,677,967 | 7/1987 | Zartman . | |

FOREIGN PATENT DOCUMENTS

| | | |
|---|---|---|
| 1182531 | 2/1985 | Canada . |
| 1205867 | 6/1986 | Canada . |
| 1205868 | 6/1986 | Canada . |

*Primary Examiner*—Max Hindenburg

*Attorney, Agent, or Firm*—Adrian D. Battison; Stanley G. Ade; Murray E. Thrift

[57] ABSTRACT

An anchor device for mounting a temperature sensing and transmission system within the vagina of a mammalian female such as a beef cow comprises a cylindrical body formed by a thin wall having an opening at one end into which the telemetry device can be inserted. Two sets of four fingers are arranged at axially spaced positions extending outwardly from the body wall at positions spaced from the ends of the body. The fingers are relatively rigid and extend substantially directly outwardly substantially at right angles to the longitudinal axis. Each finger has a convex outer end which is arranged to engage the inner wall of the vagina and is arranged to avoid irritation of the flesh. The relatively large spaces between the fingers allows the ready communication of fluids longitudinally of the vagina as are required for normal functioning and for artificial insemination.

12 Claims, 3 Drawing Sheets

METHOD OF USING A SUPPORT ANCHOR FOR THE VAGINA OF A MAMMALIAN FEMALE

BACKGROUND OF THE INVENTION

This invention relates to an anchor device for supporting an element within the vagina of a mammalian female.

The present invention is particularly, but not exclusively concerned with the mounting in a suitable location on a mammalian female of a temperature monitoring device which can be used to detect temperature changes indicative of estrus of the female to enable accurate timing of artificial insemination.

However the anchor device with which the present invention is concerned may be used for other purposes such as other telemetry devices or for drug release.

It is known that temperature changes can be used to predict the occurance of estrus in mammalian females. In cows a rise in temperature of 0.3 to 0.8 degrees celcius is usually found at estrus. Estrus has a duration of eight to twelve hours and occurs at roughly twenty one day intervals. If the cow does not conceive at first insemination, it is necessary to inseminate again at successive estrus until the cow does conceive. For this reason it is often necessary to continuously monitor the vagina temperature of the cow (to predict the occurance of estrus) for prolonged periods of time. Because vagina temperature varies due to factors other than estrus, it is necessary to compare vagina temperature to the rolling average of temperature for some days previous in order to make a decision as to whether the rise in temperature is significant.

Other devices are available for detecting estrus and one example comprises a pedometer which detects increases in animal movement which are also indicative of estrus. Other techniques for detection in the past have involved visual observation of the cow behaviour or the use of marker bulls which result in colour marking of the cow upon mounting by the bull during estrus. In some cases the level of progesterone hormone in the milk can be indicative of estrus.. Also some milking machines measure milk temperature and some claims are made that milk temperature can be used to predict the time of estrus. No commercial use of this method has apparently occurred.

Attempts have been made to manufacture an anchor device which can be located within the vagina of the mammalian female such as a cow. One example is shown in U.S. Pat. No. 4,387,724 (Zartman) and in U.S. Pat. No. 4,377,157 also of Zartman. These devices cannot support a telemetry device of a type comprising a radio transmitter of sufficient dimension to provide a receivable signal over a sufficient distance to enable continual monitoring of the temperature. A further device is known as the Heigro device (Agrophysics, San Francisco, Calif.) which was designed for long term residence in the heifer's vagina. In addition to these devices being unable to receive and support an element of sufficient size for remote telemetry, there is a severe danger that these devices will be expelled and in some examples up to fourty percent were expelled within the first month. It will be appreciated that in order for these devices to be commercially viable, it is necessary that the device remain in place for significant periods of time and also be reusable without the loss or damage which can occur if the device is expelled.

Up till now, therefore, there has been no anchor device available which enables the relatively large transmitter necessary for continual monitoring to be mounted within the vagina of the mammalian female and which enables the device to remain in position for extended periods of time.

In some cases this problem has been overcome by surgical techniques in which the telemetry device is mounted within an incision in the animal. This is of course however disadvantageous in that the surgical invasion is expensive and time consuming and is open to infection.

Attempts have also been made to detect temperature changes by a measuring device attached to the ear skin of the animal. However it has not been proven that ear skin temperature can be used to effectively detect estrus.

SUMMARY OF THE INVENTION

It is one objective of the present invention, therefore to provide an anchor device for anchoring an element within the vagina of a mammalian female.

According to the invention, therefore, there is provided an anchor device for supporting an element within the vagina of a mammalian female, the device comprising a body portion having an opening therein for receiving the element to be supported and a plurality of flexible fingers projecting outwardly from the body portion, the fingers being arranged at angularly spaced positions around the body portion, the fingers having outer ends arranged to engage the vaginal wall without irritation, the fingers being spaced and arranged so as to hold the body portion at a position spaced from the vaginal wall and to allow material to pass longitudinally out of the vagina past the body portion between the fingers.

The vaginal anchor can be manufactured from a suitable flexible plastics material such as plastisol which is used to define a central body portion which encases a radio transmitter to allow permanent placement of the radio transmitter in the vagina of a cow or other mammalian female such as the horse, pig and in some cases more exotic zoological animals. The device generally consists of a hollow body from which a numerous flexible finger projections protrude. The finger projections are situated in such a manner that the anchor exterior shape is essentially spherical. In one example the finger projections are eight millimeters in diameter and the finger projection tips are convexly rounded. In one example the length of the fingers can be 30 to 34 millimeters. In a second example the finger projections are of 24 to 28 millimeters in length. The length of the fingers will of course vary depending upon the dimensions of the animal involved.

The anchor is manufactured from plastisol or other residual plastics material which is non irritating to the animal tissue.

One example of a suitable radio transmitter is manufactured by Wildlife Materials Inc. of Carbondale Ill., and this can be directly inserted into the hollow body of the anchor as a sliding fit. In the insertion process, the anchor is soaked for twenty minutes in a sterilizing solution and is warmed to body temperature to increase the finger projection flexibility. The device is then manually inserted into the cow vagina. For insertion the technician encases the anchor transmitter in the hand with the finger projections bent rearwardly toward the body of the anchor. The anchor is then deposited in the vagina against or adjacent the cervix. When released the fingers return by natural elasticity to the initial position projecting generally directly outwardly from the central body.

The use of the finger projections are non-irritating to animal tissue within the vagina and also prevents the expulsion of the device.

Each radio transmitter is designed to emit a unique radio signal which indicates the cow identity and the vaginal temperature. These signals are emitted at five minute intervals and are received by a receiver/computer unit which makes the record of the cow identity, temperature and time of day that the signal is received. The temperature values are used to predict the occurance of estrus in the cow. A rise in temperature of 0.3 to 0.8 degrees celcius is usually found at estrus. When estrus is detected, the cow is inseminated by artificial insemination.

The positioning, spacing and length of the fingers supports the body away from the wall of the vagina allowing material to pass through the vagina longitudinally between the fingers. In this way the normal flow of materials such as mucous in the outward direction can occur and in addition the artifical insemination can be carried out with the device in place.

The anchor device can be used with a telemetry element to measure vaginal temperature of dairy cows and other mammals for estrus detection and also for reasons other than the detection of estrus. Continuous temperature measurement of financially valuable female livestock, for example race horses, could help in the detection of disease at the sub clinical level. Also the device could be used as a parturition alarm. With the onset of labour the transmitter and anchor unit would be expelled from the vagina and the resulting dramatic drop in recorded temperature could trigger an alarm which would alert the animal attendant. This will be particularly useful in a swine operation or where any financially valuable animal is about to deliver and where an unassisted labour is undesirable.

One or more embodiments of the invention will now be described in conjunction with the accompanying drawings.

BRIEF DESCRIPTION OF THE DRAWINGS

In the drawings like characters of reference indicate corresponding parts in the different figures.

DETAILED DESCRIPTION

Figure 1:
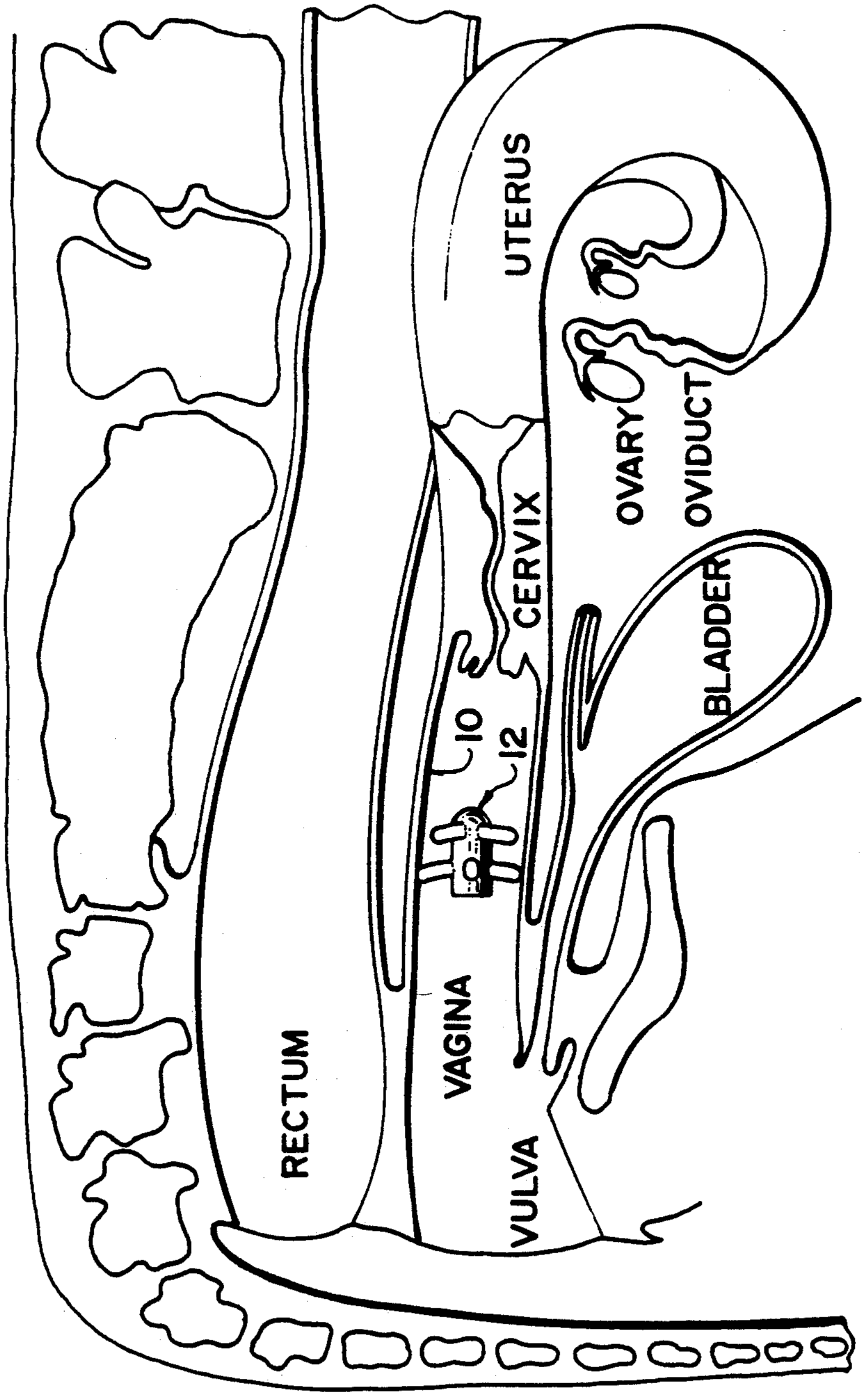
FIG. 1 is a schematic illustration of the anatomy of a dairy cow showing the device according to the present invention insitu within the vagina.

The anatomy of the dairy cow shown in FIG. 1 and the various elements of the anatomy are indicated on the schematic illustration. The vagina includes a vaginal wall 10 leading to the cervix and the device according to the present invention is generally indicated at 12 and is mounted within the vagina in contact with the vaginal wall at a position partway along the vaginal wall and spaced outwardly from the cervix.

Figure 2:
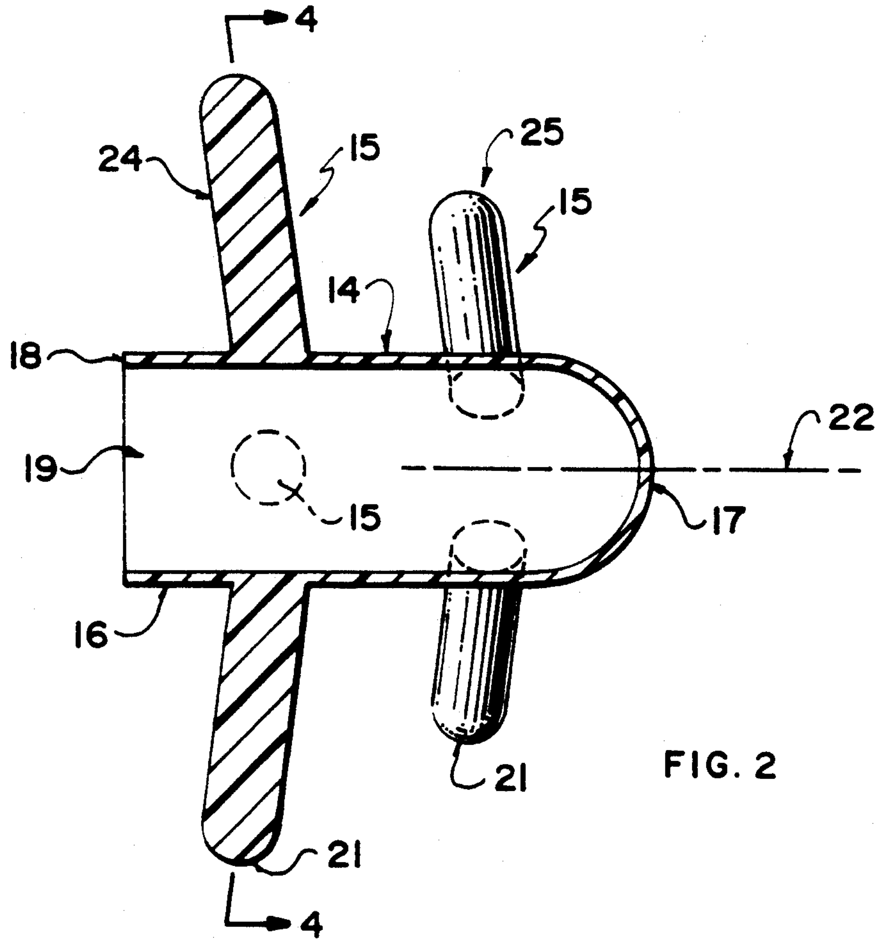
FIG. 2 is a longitudinal cross-sectional view through the anchor device itself with the telemetry element omitted.
Figure 3:
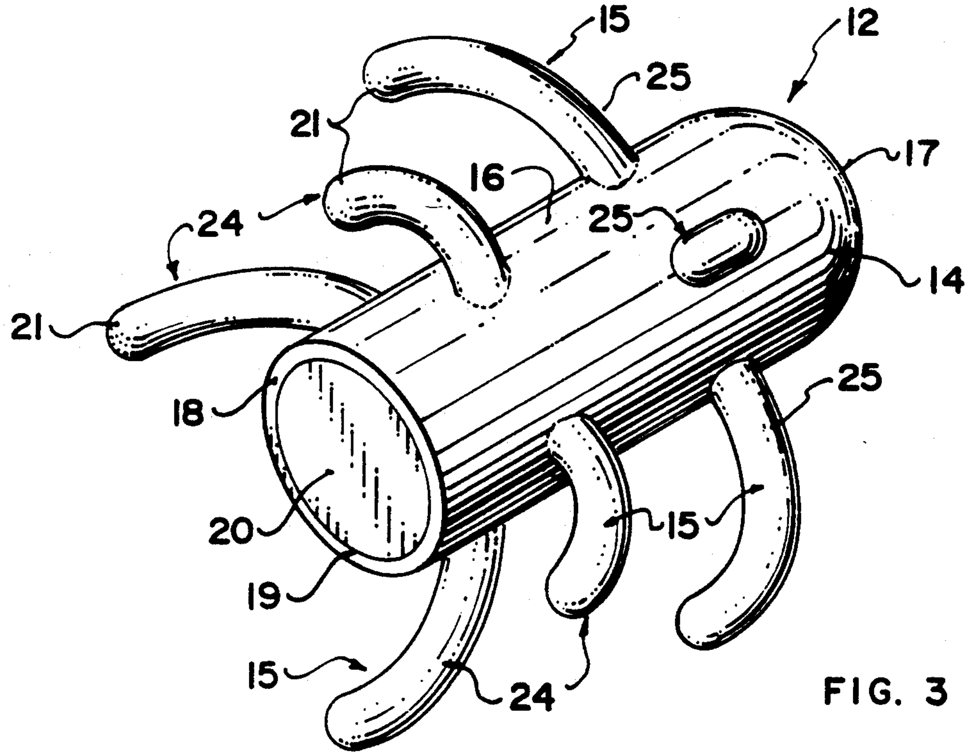
FIG. 3 is an isometric view of the anchor device and telemetry element with projecting fingers in a flexed condition allowing for insertion of the device into the required location.
Figure 4:
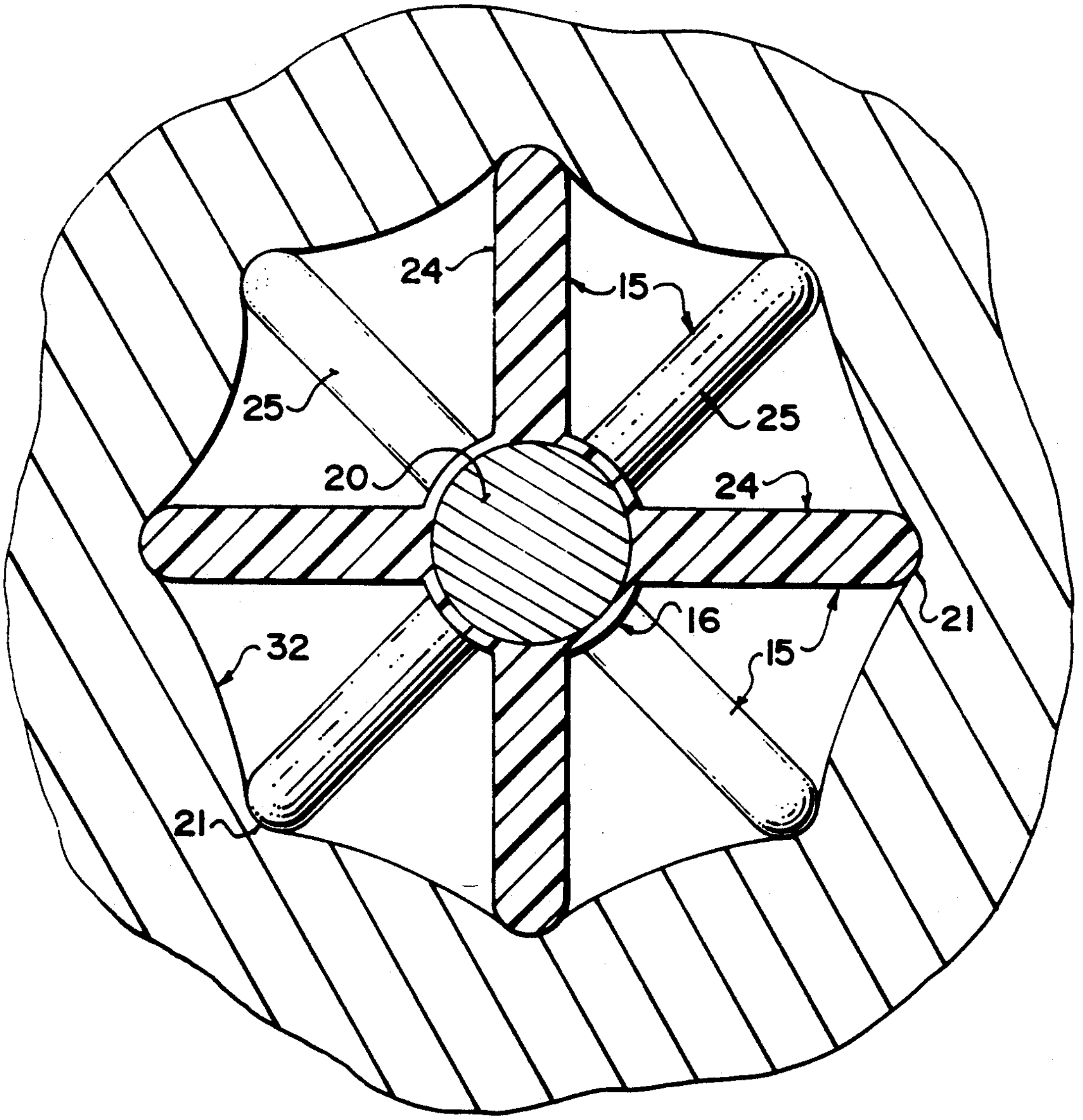
FIG. 4 is a cross sectional view along the lines 4—4 (FIG. 3) showing the device in position within the vagina.

The device is shown best in FIGS. 2, 3 and 4 and comprises a main body portion 14 and a plurality of outwardly projecting fingers 15.

The main body portion 14 comprises an elongate cylindrical body of a thin wall 16 generally of circular cross-section as best shown in FIG. 4. The cylindrical wall 16 includes a forward end 17 and a rearward end 18. The forward end 17 is generally convex in shape and is fully closed. The rearward end 18 defines an opening 19 into which the telemetry element 20 can be inserted as a sliding fit within the cylindrical wall 16.

The telemetry element 20 is of a conventional design manufactured by Wildlife Materials Inc., Carbondale, IL which is commercially available. The telemetry element includes a temperature sensing device, an encoding system for transmitting a signal indicative of the animal concerned together with a signal indicative of the detected temperature, and a transmission system of a type for transmitting the signal over a distance of at least of the order of fifty and preferably of the order of 60 meters. The telemetry device yet further includes the necessary battery power and an antenna for the long distance transmission system. The electronic components are potted within a suitable potting material so as to form a device which is resistant to corrosion or contamination by moisture. The complete element defines a generally cylindrical body of a length of the order of 2.5 inches and a diameter of the order of one inch.

The dimensions of the cylindrical wall 16 are arranged to just receive the element as a sliding fit therein in contact with the inside surface of the wall 16 so as to hold the element permanently in place but removable from the hollow interior of the body as required for service.

The hollow wall 16 of the body is formed from a suitable plastics material such as plastisol which is a medically acceptable plastics material and provides a relatively flexible structure in the form of a collapsible sheath which can to some extent stretch as required to receive the element therein and to allow some flexing of the fingers as discussed hereinafter.

Each of the fingers 15 is generally cylindrical in shape of a circular cross section. Each of the fingers is attached at its inner end to the wall 16. In a prototype laboratory model of the device, the fingers can be attached by the provision of a flat disc at the inner end of each of the fingers with the finger passing through a hole in the wall 16 to allow the disc to abut against the inside surface of the wall. In a preferred model suitable for commercial manufacture, the fingers are integrally molded with the wall 16 so that the base of the finger is integral with the wall allowing some flexing of the finger by distortion of the wall 16.

Each of the fingers 15 is similarly formed by molding from a suitable plastics material such as plastisol which again allows some flexibility and provides a medically acceptable plastics material for contacting the tissue of the animal.

Each of the fingers 15 is somewhat rigid so that it allows only a limited amount of flexing from the normal substantially radial position to a flexed position shown in FIG. 3 in which the finger turns approximately through 90° to lie closer to the body 14 but spaced outwardly therefrom.

Each of the fingers 15 includes a convexly curved outer end 21. The convexly curved end 21 lies transverse to a longitudinal axis of the finger so that with the finger extending generally radially outwardly from the cylindrical body, the longitudinal axis of the finger lies substantially at right angles to an axis 22 of the body with the outer convex surface 21 lying generally parallel to the axis 22. Thus the fingers stand generally outwardly from the body with the outer convex ends 21 in contact with the inner surface 32 of the vagina of the animal.

As shown in FIGS. 2 and 4, in the normal inserted position, the fingers stand substantially straight out from the body with very little flexing. Thus each finger contacts the inside surface 32 and to some extent depresses the surface 32 to engage the tissue of the animal to hold the device in place.

In one example the diameter of each of the fingers is of the order of 8 millimeters (0.3 inches) leading to a surface area at the end of the finger which is 0.071 square inches. Preferably the diameter of the outer end of the finger lies in the range $\frac{1}{8}$ to $\frac{1}{2}$ inches thus leading to a contact area lying in the range 0.0122 to 0.196 square inches. A contact area of this dimension is unlikely to lead to irritation of the surface 32 provided the length of the fingers is selected relative to the size of the animal to provide only a slight indentation of the surface but of course to maintain contact with the surface to prevent expulsion of the device.

The fingers 15 are arranged in two sets of fingers indicated generally at 24 and 25. These sets are spaced axially of the body so that one set 24 is arranged adjacent the end 18 and the second set 25 is arranged adjacent the end 17. Within each set of fingers the individual finger may vary in distance from the ends 18 and 17 with a minimum distance of $\frac{1}{2}$" and a maximum distance of 1". Because both sets are spaced inwardly from the respective end, an imaginary surface including the ends 17 and 18 of the body and the ends 21 of the fingers lies substantially on a sphere surrounding a centre of the body lying on the axis 22.

Each of the sets 24 and 25 includes four fingers arranged at right angles so that in FIG. 4 the set 24 is shown in cross section and the set 25 is shown set back from the cross section. Also as shown in FIG. 4, the fingers of the set 25 are rotated around the axis 22 by an angle of 45° so that they are offset from the fingers of the set 24.

The number of fingers in each set can be varied but a minimum of two such fingers is required to locate each end of the body relative to the surface 32 to hold the axis 22 of the body substantially centrally of the surface 32. The fingers at each position are also arranged equiangularly spaced so as to be symmetrical around the axis 22. Thus the minimum number of fingers at each position would be two arranged at 180° spacing. In the embodiment shown there are four such fingers arranged at 90° spacing. Yet further fingers could be included up to a maximum of five. However the number of fingers is maintained so that each finger is attached separately to the body 14 at the wall 16 leaving some material of the wall 16 between each finger and the next adjacent finger to allow individual flexing of the fingers. Thus the fingers are formed separately and do not form of a spider structure carried by the body. As shown in FIG. 4, therefore the bases of the fingers lie on a circle surrounding the element 20 so as to leave enough room for the element 20 to be inserted inside the fingers.

The device as described above provides an anchor device for a remote telemetry device or the like which effectively anchors the telemetry device within the vagina of the animal for use over an extended period of time without expulsion of the device by the muscular action of the animal.

The device is wholly manufactured from a medically acceptable plastics material such as plastisol. The design of the device enables the device to be manufactured with different length of fingers for different dimensions of animal. The design of the device enables a relatively large element to be received within the hollow body to allow transmission of signals over a relatively large range up to sixty meters so that the animal can be continually detected rather than detected only at specific times when it is closely adjacent a receiving station.

The limited number of large relatively rounded fingers ensures that the device while residing permanently in the vagina does not irritate the tissue of the animal which could otherwise interfere with the estrous cycle. The spacing between the fingers is relatively large both at the central body and at the surface 32 of the vagina allowing ready transmission of fluids longitudinally out of the vagina which is necessary for mucous flow and passage is also necessary for the artificial insemination process.

Although the fingers are arranged to extend outwardly from the body substantially at right angles to the axis 22, the fingers may have a slight rearward inclination as best shown in FIG. 2. This inclination lies in the range 0 to 15 degrees and may assist in preventing expulsion of the device and also in allowing flexing of the fingers in cases where the outer diameter of the fingers is slightly large for the particular animal However in all cases the outer surface of the fingers faces generally outwardly away from the body as opposed to a "christmas tree" effect.

Suitable receiving and decoding equipment can be used to analyze the data received from the animal. Each transmitter sends a unique identification signal at a common frequency. Signals are transmitted at regularly spaced time intervals much smaller than daily that is a plurality of times per hour and preferably at a time period of approximately every four minutes. A receiving antennae is placed with 60 meters of the location of monitored animals. This allows the animals to be monitored substantially continuously as opposed to daily which is only possible with short distance transmitters. In such a case the animal is only monitored as it passes a monitoring station for example at milking, in which case the detection period may be too course to detect estrus which can last less than twenty four hours. The signals are received and decoded using programs which will be apparent to one skilled in the art.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

We claim:

1. A method for supporting an element within the vagina of a mammalian female, the method comprising providing a body portion in the form of a sleeve having a first end and a second end and a peripheral wall surrounding a longitudinal axis of the sleeve and having an opening at the first end of the sleeve receiving the element supported within the sleeve so as to be wholly confined therein and a plurality of flexible fingers projecting outwardly from the body portion, arranging the fingers in a first set and a second set, the sets being axially spaced from the ends of the sleeve and from each other, arranging the fingers of each set at angularly spaced positions around the axis of the body portion, the fingers each being substantially straight so as to define a longitudinal axis of each finger arranged to extending substantially radially outwardly from the axis of the sleeve and so as to define an end surface of each finger facing outwardly along the longitudinal axis of the finger engaging the vagina wall, the end surface of each finger having a contact area which is sufficiently large to engage the vagina wall without irritation, the fingers being spaced and arranged so as to hold the body portion at a position spaced from the vagina wall and to allow material to pass longitudinally out of the vagina past the body portion between the fingers.

2. The method according to claim 1 wherein the end surface of each of the fingers is a convexly rounded end defining an area of contact with the wall greater than 0.012 sq. in..

3. The method according to claim 1 wherein the fingers are substantially cylindrical.

4. The method according to claim 3 wherein the fingers are substantially of circular cross-section.

5. The method according to claim 1 wherein a transverse width of the end of each of the fingers lies in the range ⅛ to ½ inch.

6. The method according to claim 1 wherein the body portion is formed from a thin flexible walled material from which the fingers project.

7. A method of detecting estrus in a mammalian female comprising providing a telemetry element including a temperature measuring probe and a transmitter, locating an anchor element within the vagina of the female, providing on the anchor element a main body portion, the anchor element being in the form of a sleeve having a first end and a second end and a peripheral wall surrounding a longitudinal axis of the sleeve and having an opening at the first end of the sleeve, inserting the telemetry element into the sleeve through the opening so as to be wholly confined therein, providing on the main body portion a plurality of outwardly extending fingers, arranging the fingers in a first set and a second set, the sets being axially spaced from the ends of the sleeve and from each other, arranging the fingers of each set at angularly spaced positions around the axis of the body portion, the fingers each being substantially straight in the vagina so as to define a longitudinal axis of each finger extending substantially radially outwardly from the axis of the sleeve so as to define an end surface of each finger facing outwardly along the longitudinal axis of the finger and engaging the vagina wall, the end surfaces having a contact area sufficient to engage the vagina wall without irritation, the fingers being spaced and arranged to hold the main body portion at a position spaced from the vagina wall to allow the material to pass longitudinally outwardly of the vagina, the transmitter having a range when implanted in the vagina of at least of the order of fifty meters, transmitting from the transmitter a plurality of times per hour at spaced intervals during the day information defining the female and the vagina temperature of the female, locating a detector at a position relative to the female to detect the transmissions and analyzing the transmissions to identify estrus in the female.

8. The method according to claim 7 wherein the end surface of each of the fingers is a convexly rounded end defining an area of contact with the wall greater than 0.012 sq. in..

9. The method according to claim 7 wherein the fingers are substantially cylindrical.

10. The method according to claim 7 wherein the fingers are substantially of circular cross section.

11. The method according to claim 7 wherein a transverse width of the end of each of the fingers lies in the range ⅛ to ½ inch.

12. The method according to claim 7 wherein the body portion is formed from a thin flexible walled material from which the fingers project.

* * * * *